(12) United States Patent
Jindo et al.

(10) Patent No.: US 9,228,924 B2
(45) Date of Patent: Jan. 5, 2016

(54) HOMOGENIZER

(71) Applicant: SYSMEX CORPORATION, Kobe-shi, Hyogo (JP)

(72) Inventors: Katsuhiko Jindo, Kobe (JP); Yoshinori Ooi, Kobe (JP); Shoichiro Asada, Kobe (JP); Daijyu Obinata, Shiojiri (JP)

(73) Assignee: SYSMEX CORPORATION, Hyogo (JP)

( * ) Notice: Subject to any disclaimer, the term of this patent is extended or adjusted under 35 U.S.C. 154(b) by 21 days.

(21) Appl. No.: 13/971,451

(22) Filed: Aug. 20, 2013

(65) Prior Publication Data

US 2014/0056783 A1  Feb. 27, 2014

(30) Foreign Application Priority Data

Aug. 21, 2012 (JP) ................. 2012-182320

(51) Int. Cl.
  *A61B 10/00* (2006.01)
  *G01N 1/28* (2006.01)
  *C12M 1/33* (2006.01)

(52) U.S. Cl.
  CPC ............ *G01N 1/28* (2013.01); *C12M 45/02* (2013.01); *G01N 1/286* (2013.01)

(58) Field of Classification Search
  CPC .......... C12M 33/00; G01N 1/00; A61B 10/00
  See application file for complete search history.

(56) References Cited

U.S. PATENT DOCUMENTS 4,084,757 A * 4/1978 Rakitin et al. ................ 241/301
8,216,528 B2 * 7/2012 Shomi ............................ 422/536

FOREIGN PATENT DOCUMENTS

JP    2008-212019       9/2008
WO    2005047866 A1     5/2005

* cited by examiner

*Primary Examiner* — Jyoti Nagpaul
(74) *Attorney, Agent, or Firm* — Sughrue Mion, PLLC

(57) ABSTRACT

Disclosed is a homogenizer comprising: a crushing part having a blender for crushing a tissue sample in a container; a rotation driver configured to rotate the blender in contact with the tissue sample; and an absorbing part for absorbing a pressure applied to the tissue sample, which is caused when the blender comes into contact with the tissue sample.

11 Claims, 13 Drawing Sheets

F I G. 1 1
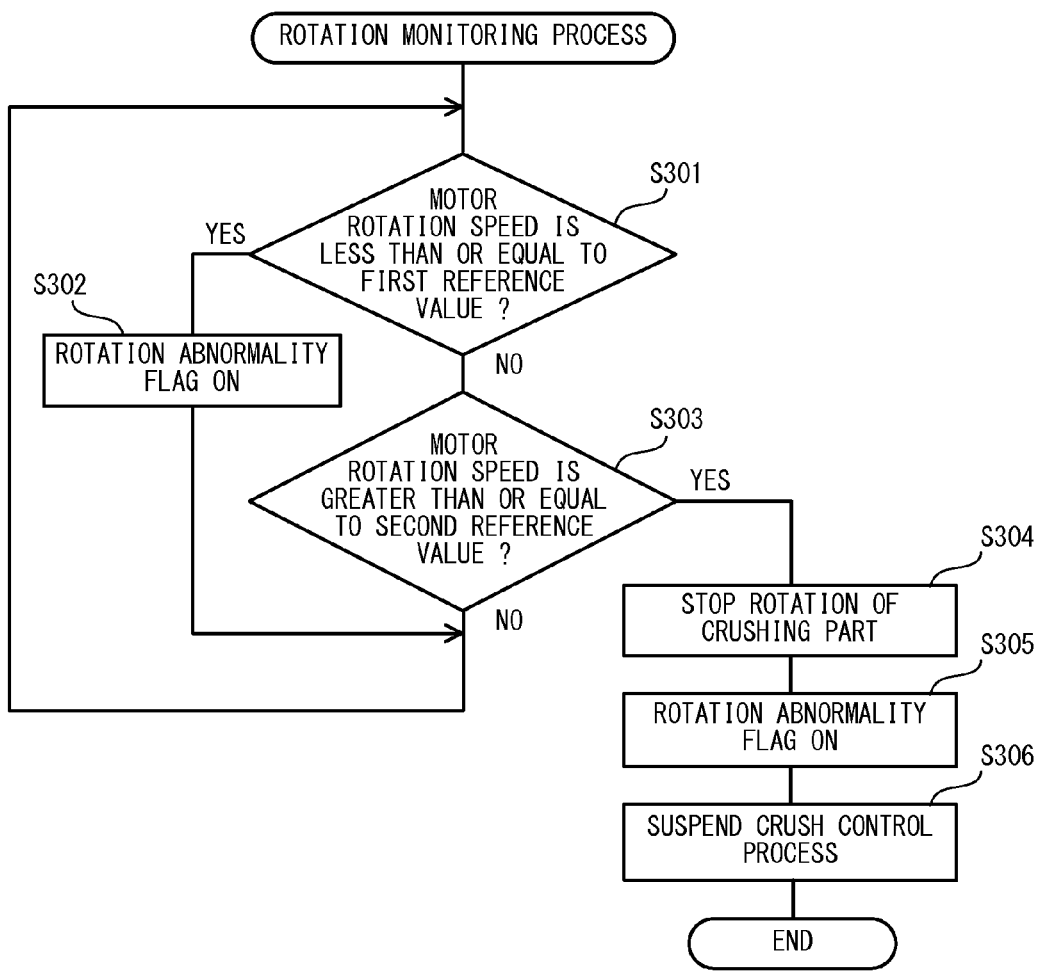

F I G. 13
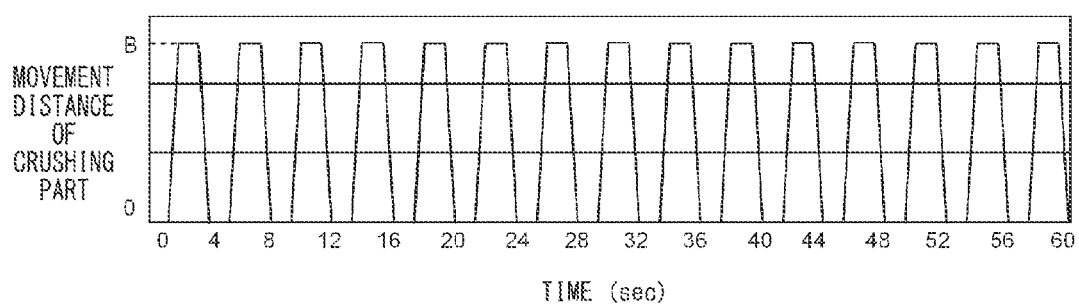

HOMOGENIZER

TECHNICAL FIELD

The present invention relates to a homogenizer for crushing tissue samples collected from human beings, animals, or plants.

BACKGROUND ART

In recent years, genetic tests have rapidly prevailed in the field of clinical diagnoses. A genetic test is a test that examines, for clinical purposes, whether there is a mutation or karyotype that is relevant to a genetic disease by analyzing nucleic acids or chromosomes. Examples of a genetic test include a test that determines whether there is a nucleic acid derived from cancer cells in a tissue sample resected from an organism. The test process includes three major process steps of preprocessing, nucleic acid amplification, and detection.

In the preprocessing, a crushing process to crush (homogenize) a tissue sample is performed. As one method of this crushing process, there is widely used a crushing method in which a crushing tool called a blender is brought, while being rotated, into contact with a tissue sample. U.S. Pat. No. 8,216,528 discloses a sample processing device which crushes a tissue sample by the above crushing method. The sample processing device disclosed in U.S. Pat. No. 8,216,528 includes a crushing tool composed of an inner crushing member and an outer side crushing member which is a tubular body capable of housing the inner crushing member therein. The sample processing device is configured such that a tissue sample (lymph node) is crushed to a predetermined size, by the inner crushing member of the crushing tool being repeatedly moved upward and downward while being rotated by a motor.

In the sample processing device disclosed in U.S. Pat. No. 8,216,528, when the crushing tool is moved downward, the tip of the crushing tool is pressed against a tissue sample, and in this state, the inner crushing member of the crushing tool is rotated, whereby the tissue sample is crushed. Here, it is known that a cancerous lymph node is harder than a non-cancerous lymph node. When crushing a hard lymph node, if the inner crushing member of the crushing tool is pressed with an excessive force, there may be a case where the inner crushing member bites into the lymph node to get stuck therein and becomes unable to rotate. This may result in a crushing failure of the tissue sample of the lymph node.

SUMMARY OF THE INVENTION

A first aspect of the present invention is a homogenizer comprising: a crushing part having a blender for crushing a tissue sample in a container; a rotation driver configured to rotate the blender in contact with the tissue sample; and an absorbing part for absorbing a pressure applied to the tissue sample, which is caused when the blender comes into contact with the tissue sample.

A second aspect of the present invention is a homogenizer comprising: a crushing part having a crushing member for crushing a tissue sample in a container, by rotating in contact with the tissue sample; a rotation driver configured to rotate the crushing part; and an adjusting part for adjusting, when the crushing part comes into contact with the tissue sample in the container, a pressing force applied to the tissue sample.

A third aspect of the present invention is a homogenizer comprising: a crushing part having a blender at a tip in a longitudinal direction thereof; a movement part configured to move the crushing part in the longitudinal direction to insert the blender into a container; and a rotation driver configured to rotate the blender, wherein the blender is biased toward its tip end, and the crushing part is configured to contract when a force exceeding a tension of the bias is applied to the crushing part in an opposite direction to a moving direction of the crushing part.

BRIEF DESCRIPTION OF THE DRAWINGS

FIG. 11 is a flow chart showing a procedure of a rotation monitoring process;

FIG. 13 is a graph showing a relationship between a movement distance of the crushing part and time in a crushing operation.

DESCRIPTION OF EMBODIMENTS

Hereinafter, an embodiment of the present invention will be described with reference to the drawings.

<Structure of Homogenizer>

Figure 1:
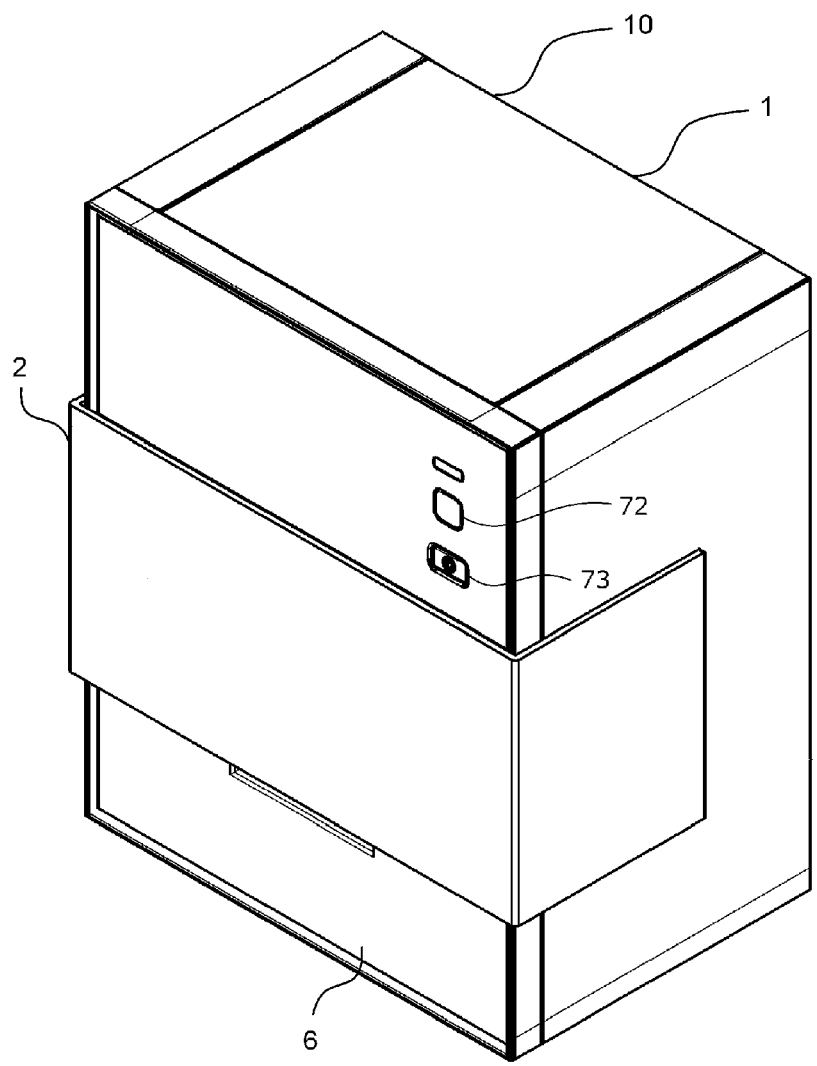
FIG. 1 is a perspective view showing an outer view of a homogenizer according to an embodiment.

FIG. 1 is a perspective view showing an outer view of a homogenizer according to the present embodiment. A homogenizer 1 according to the present embodiment is an apparatus that is installed mainly in a pathological laboratory of a hospital and that is configured to crush, in a buffer solution, a tissue sample collected from a patient in an operating room. The homogenizer 1 includes an apparatus body 10 having a substantially rectangular parallelepiped shape, and a cool box 4 (see FIG. 2) detachable from the apparatus body 10. The apparatus body 10 is provided with a cover 2 which covers a part of the front face thereof. The cover 2 is slidable in the up-down direction so as to be able to be opened and closed. FIG. 1 shows a state where the cover 2 is closed.

Figure 2:
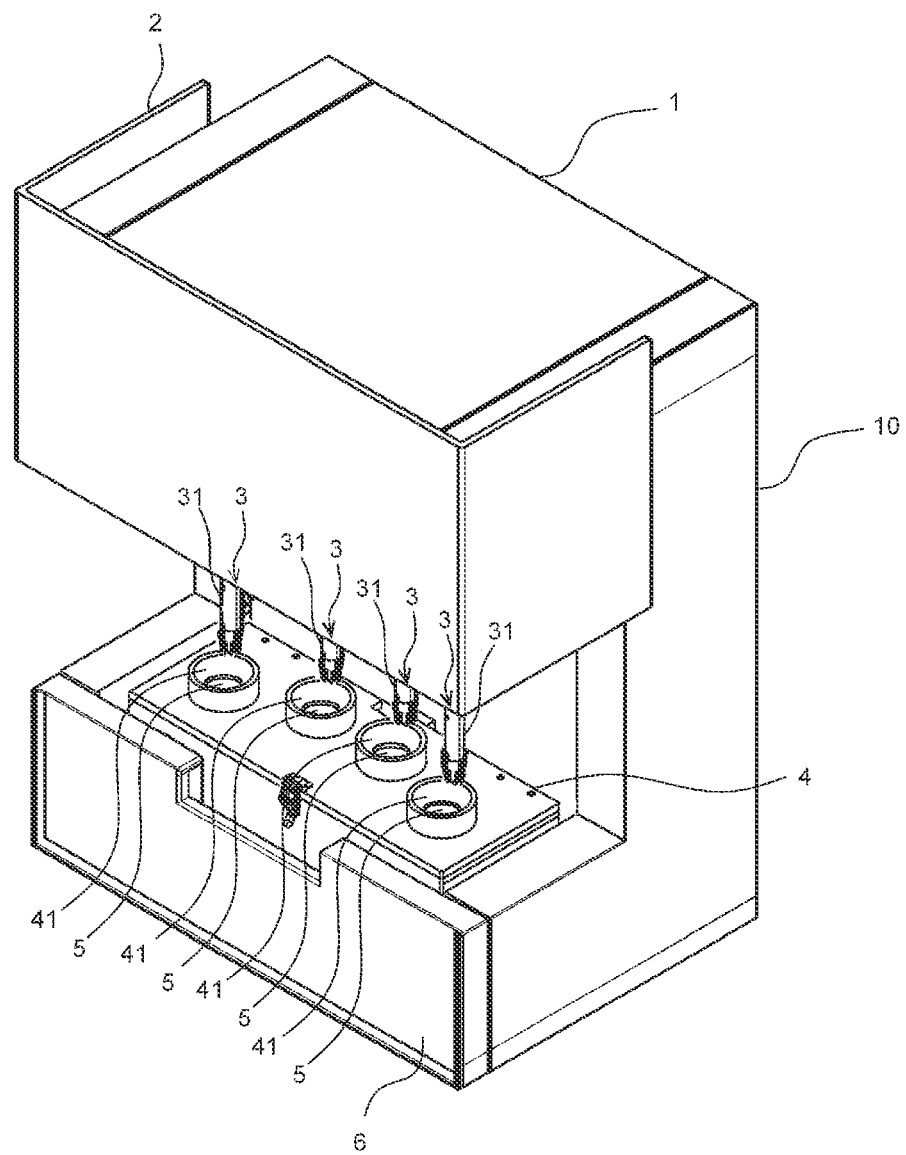
FIG. 2 is a perspective view showing an outer view of the homogenizer with its cover open.

When the closed cover 2 is slid upward, the cover 2 is opened. FIG. 2 is a perspective view showing an outer view of the apparatus body 10 with the cover 2 open. When the cover 2 is open, a middle portion in the up-down direction of the apparatus body 10 is exposed. This middle portion has a shape whose front side is recessed. In this recessed portion, four crushing parts 3 are provided. Each crushing part 3 includes a rotation mechanism section provided in the ceiling portion for the recess, and a blender 31 which is a crushing tool for crushing a tissue sample. Each blender 31 is detachable from the rotation mechanism section and disposable, in order to prevent contamination.

Figure 3:
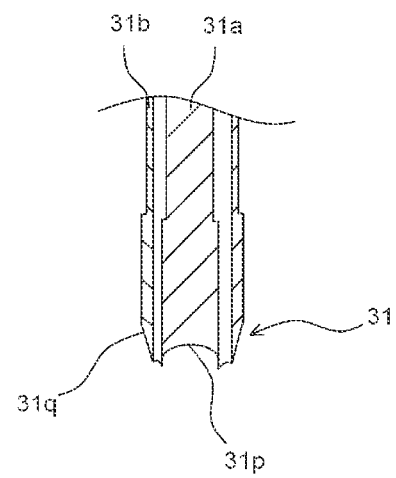
FIG. 3 is a fragmentary side sectional view showing a structure of a blender.

Each blender 31 is a plastic member having a substantially cylindrical shape, and is configured to be attachable, at an upper end portion thereof, to its corresponding rotation mechanism section. Accordingly, the blender 31 is attached to the rotation mechanism section in such a manner as to be suspended from the ceiling portion of the recess. FIG. 3 is a fragmentary side sectional view showing a structure of a blender 31. As shown in FIG. 3, the blender 31 has a double structure, and includes an inner part 31a and an outer part 31b, each having a cylindrical shape. The lower ends of the inner part 31a and the outer part 31b are provided with blades 31p and 31q for crushing a tissue sample, respectively. The rotation mechanism section has built therein a blade rotating motor 32 being a brushless DC motor (see FIG. 8). In the blender 31 attached to the rotation mechanism section, only the inner part 31a is rotated by the blade rotating motor 32. Accordingly, the blade 31p (hereinafter, referred to as "inner blade") of the inner part 31a and the blade 31q (hereinafter, referred to as "outer blade") of the outer part 31b are rotated coaxially relative to each other, whereby the tissue sample which is brought into contact with the inner blade 31p and the outer blade 31q is cut.

Below the crushing parts 3, the cool box 4 is arranged. The cool box 4 is capable of holding four sample containers 5. Each sample container 5 contains a buffer and a tissue sample collected from a subject. At positions on the upper surface of the cool box 4 and immediately below the crushing parts 3, four openings 41 are provided, respectively. The apparatus body 10 includes a blade raising/lowering motor 33 (see FIG. 8) being a brushless DC motor. When the blade raising/lowering motor 33 is driven, the crushing parts 3 are raised/lowered. When the crushing parts 3 are lowered due to the blade raising/lowering motor 33, the blenders 31 are inserted into the openings 41 respectively.

Figure 4:
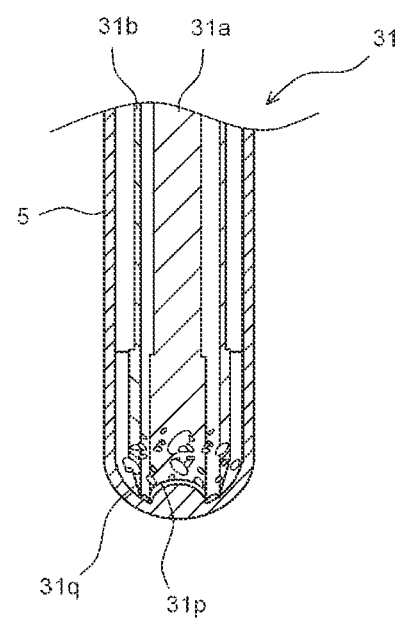
FIG. 4 is a fragmentary side sectional view of the blender for describing crushing of a tissue sample performed by the blender.

The sample containers 5 are arranged below the openings 41. By being lowered, the blenders 31 can enter the insides of the sample containers 5 through the openings 41 respectively. FIG. 4 is a fragmentary side sectional view of a blender 31 for describing crushing of a tissue sample performed by the blender 31. When the blender 31 enters the inside of the sample container 5, the tip of the blender 31 is lowered to the vicinity of a bottom portion of the sample container 5. By the inner blade 31p and the outer blade 31q rotating relative to each other in this state, the tissue sample in the sample container 5 is crushed.

Figure 5:
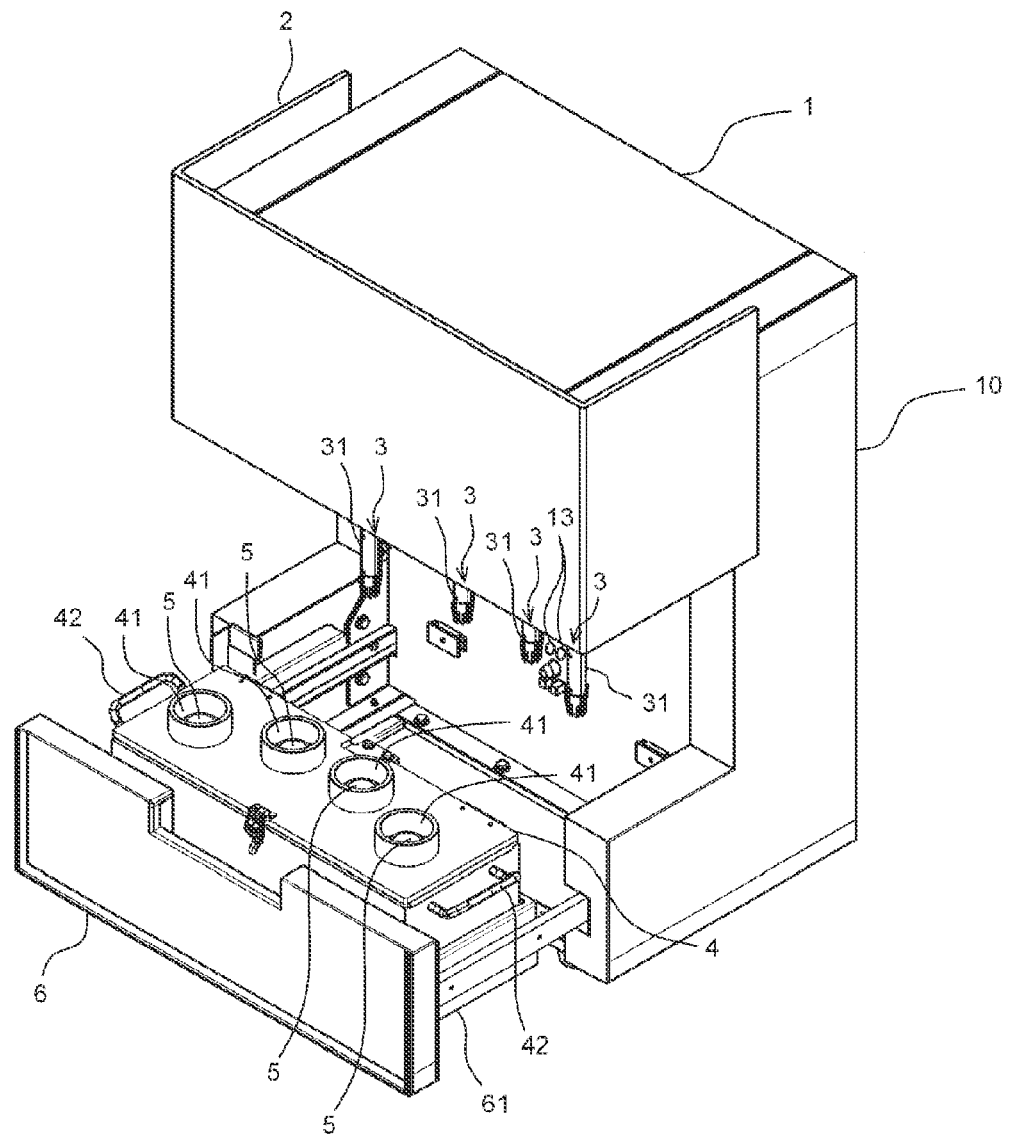
FIG. 5 is a perspective view showing an outer view of the homogenizer with a setting part drawn out.

The lower part of the apparatus body 10 has a drawer-like shape, and can be drawn forward. FIG. 5 is a perspective view showing a state where the lower part of the apparatus body 10 is drawn out. The lower part of the apparatus body 10 serves as a setting part 6 in which a user sets the cool box 4. The setting part 6 is slidable by means of a rail in the front-rear direction.

When the setting part 6 is drawn out forward, the user can mount/remove the cool box 4 on/from the setting part 6. The cool box 4 has a rectangular parallelepiped shape which is long in the substantially left-right direction. The cool box 4 includes handles 42 at respective side ends thereof. The setting part 6 is provided with a mounting part 61 on which to mount the cool box 4. The mounting part 61 has a quadrangle-dish-like shape slightly larger than the bottom portion of the cool box 4. On the mounting part 61, the cool box 4 can be mounted.

The cool box 4 has a rectangular parallelepiped box shape. On the upper surface of the cool box 4, the four openings 41 are provided. Outer two openings 41 are arranged further forward than inner two openings 41. That is, the inner two openings 41 are arranged side by side along the left-right direction, and the rightmost opening 41 and the leftmost opening 41 are arranged at positions further forward than those of the inner two openings 41. The cool box 4 is configured to hold therein crushed ice (ice crushed into particles having diameter of about 1 mm to 1 cm) as a refrigerant, and four sample containers 5 can be held in the cool box 4 as described above. Accordingly, the tissue sample and the lysate inside the sample containers 5 can be kept cool in the cool box 4.

Figure 6:
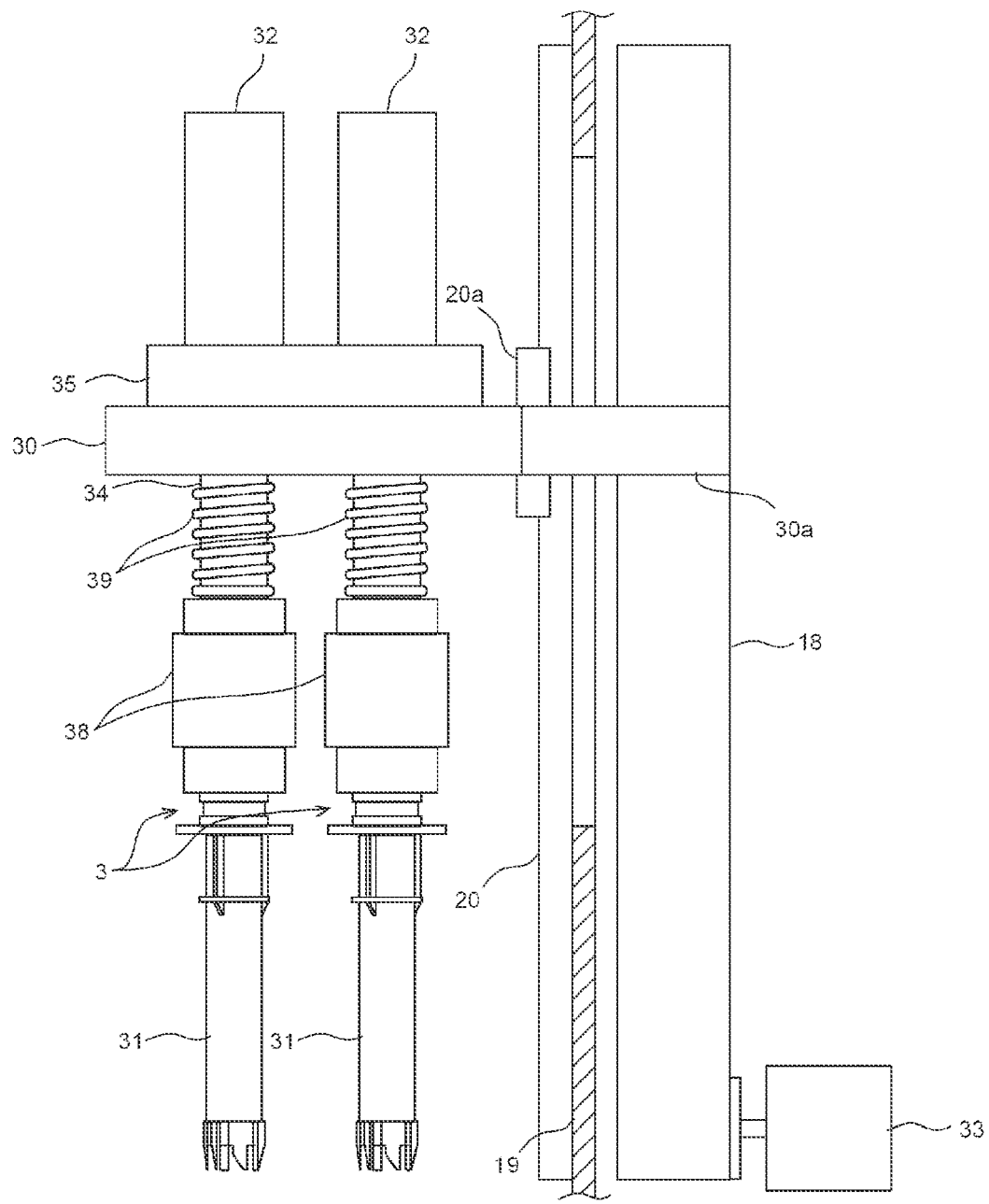
FIG. 6 is a side view showing structures of a crushing part, a support part, and a raising/lowering mechanism section.
Figure 7A:
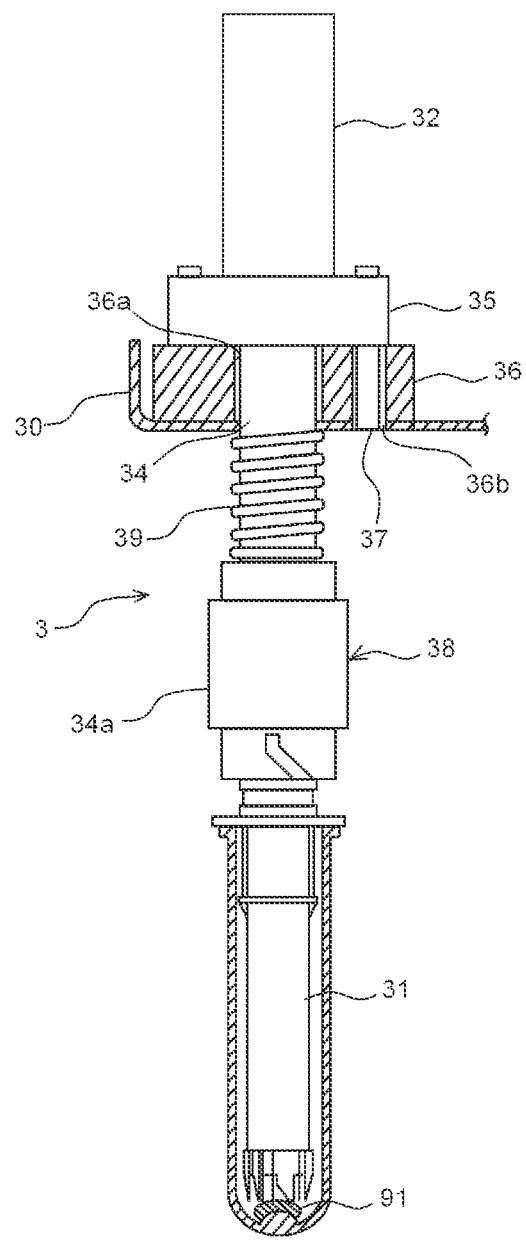
FIG. 7A is a fragmentary side sectional view showing structures of the crushing part and the support part.

The structure of each crushing part 3 is described in detail. FIG. 6 is a side view showing the structure of the crushing part 3. The crushing part 3 includes a rotation mechanism section 38 and the blender 31 detachable to the lower end of the rotation mechanism section 38. At the upper end of the rotation mechanism section 38, the blade rotating motor 32 is provided. By the blade rotating motor 32 being driven, the inner blade 31p of the blender 31 connected to the rotation mechanism section 38 is rotated. Moreover, the four crushing parts 3 are supported by one plate-like support part 30. FIG. 7A is a fragmentary side sectional view showing the structure of the crushing part 3. The rotation mechanism section 38 includes a shaft part 34 having a cylindrical shape. On the other hand, the support part 30 is provided with four support blocks 36 each having an annular shape. A hole 36a is provided in a center portion of each support block 36, and the shaft parts 34 pass through these holes 36a, respectively. The diameter of the shaft part 34 is slightly smaller than the diameter of the hole 36a, which allows the rotation mechanism section 38 to move in the up-down direction relative to the support part 30.

Below the blade rotating motor 32, a stopper 35 having a disk-like shape is provided. The shaft part 34 described above is provided so as to extend downward from this stopper 35. The stopper 35 is arranged on the upper side of the support block 36. By the upper surface of the support block 36 and the lower surface of the stopper 35 abutting against each other, the crushing part 3 is prevented from falling off from the support part 30. Further, the support block 36 is provided with another hole 36b passing therethrough in the up-down direction, and a guide pin 37 extended downward from the lower surface of the stopper 35 is inserted into this hole 36b. Accordingly, the crushing part 3 is prevented from rotating relative to the support part 30.

A spring 39 is wound around the shaft part 34. Below the shaft part 34, an attachment part 34a having a diameter larger than that of the shaft part 34 is provided. The attachment part 34a is configured such that the blender 31 is detachable from the attachment part 34a. The upper end of the spring 39 abuts against the lower surface of the support part 30, and the lower end of the spring 39 abuts against the upper end surface of the attachment part 34a. The spring 39 biases the attachment part 34a in the lower side. Accordingly, when the blender 31 is attached to the attachment part 34, the blender 31 is biased to the side of its tip end.

The apparatus body 10 includes a raising/lowering mechanism section 18 (see FIG. 6) which moves the support part 30 in the up-down direction. The raising/lowering mechanism section 18 is provided on the side opposite to the crushing parts 3 relative to a wall part 19 of the apparatus body 10, that is, the raising/lowering mechanism section 18 is provided at the rear of the wall part 19. Thus, the wall part 19 prevents the raising/lowering mechanism section 18 from being seen from outside. The raising/lowering mechanism section 18 includes a belt and a pulley which is driven by the blade raising/lowering motor 33. A coupling member 30a is extended to the rear of the support part 30. The coupling member 30a is connected to the raising/lowering mechanism section 18 through an opening that is long in the up-down direction provided in the wall part 19. That is, the support part 30 is coupled to the raising/lowering mechanism section 18 via the coupling member 30a. Thus, by the blade raising/lowering motor 33 being driven, the support part 30 can be moved in the up-down direction. Further, a rail 20 being a direct-acting guide is attached to the wall part 19, and a moving element 20a of the direct-acting guide movable along the rail is attached to the support part 30. Accordingly, movement of the support part 30 in the up-down direction is guided.

When the support part 30 is moved in the up-down direction by the raising/lowering mechanism section 18, the four crushing parts 3 supported by the support part 30 are also moved in the up-down direction, along with the support part 30. Therefore, when the support part 30 is moved downward from a state where the crushing parts 3 are located above the sample containers 5, the blenders 31 are inserted into the sample containers 5, the blade tips of the blenders 31 are pressed against the tissue samples, and then the tissue samples are crushed, respectively.

A relative movement between the crushing parts 3 and the support part 30 is described. As described above, each crushing part 3 is supported by the support part 30 so as to be movable in the up-down direction. FIG. 7A shows a state where the crushing part 3 is at the lowest position relative to the support part 30. As shown in FIG. 7A, when the lower surface of the stopper 35 abuts against the upper surface of the support block 36, the downward movement of the crushing part 3 relative to the support part 30 is accordingly limited. In addition, the compression spring 39 is applying a force in directions in which the support part 30 and the attachment part 34a are repelled from each other, whereby the lower surface of the stopper 35 is pressed against the upper surface of the support block 36. Accordingly, the crushing part 3 is as a whole biased to expand in longitudinal direction.

Figure 7B:
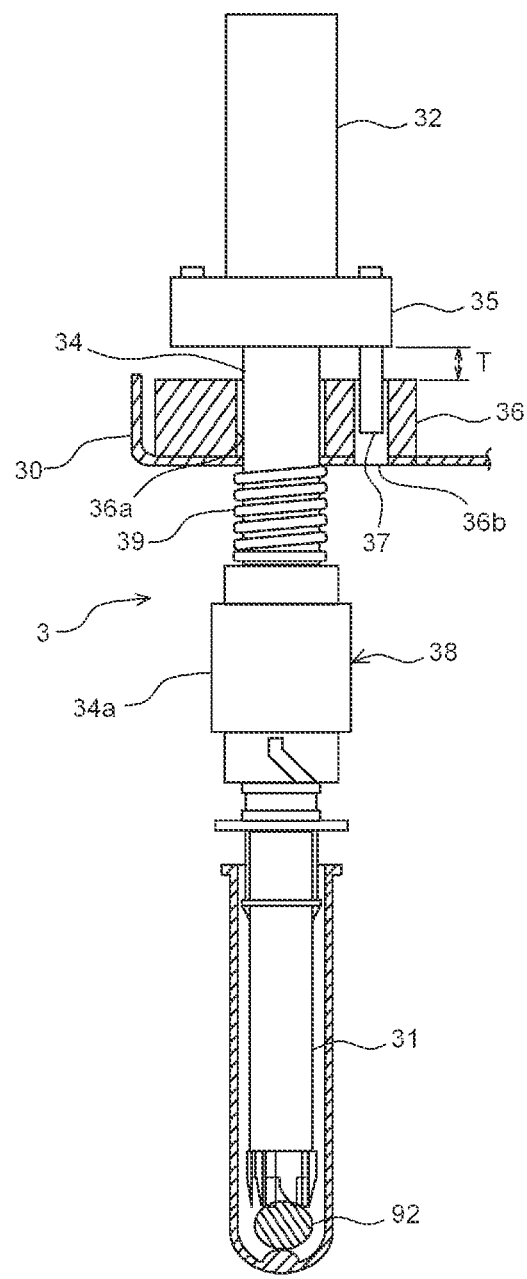
FIG. 7B is a fragmentary side sectional view showing structures of the crushing part and the support part.

When the blender 31 is pressed against a tissue sample 91, an upward force acts on the crushing part 3. As a result, the spring 39 is compressed, and the crushing part 3 is moved upward relative to the support part 30. FIG. 7B is a fragmentary side sectional view of the crushing part 3 showing a state where the crushing part 3 has been moved upward relative to the support part 30. As shown in FIG. 7B, when the upward force acts on the crushing part 3, the spring 39 is compressed and the shaft part 34 slides inside the hole 36a of the support block 36, whereby the stopper 35 is separated from the support block 36. In a case where the crushing part 3 has been moved upward by a distance T relative to the support part 30, a compressive force F generated in the spring 39 satisfies $F = k \cdot T$. Here, k is the spring constant of the spring 39. That is, by the distance T in proportion to the pressing force F applied to the blender 31, the spring 39 is compressed and the crushing part 3 is moved upward.

When the support part 30 is lowered by the raising/lowering mechanism section 18, the blender 31 comes into contact with the tissue sample 91 contained in the sample container 5. Then further the crushing part 3 is lowered. In a case where the tissue sample is soft, the tissue sample 91 deforms by being pressed by the blender 31. Accordingly, the blade tip of the blender 31 deeply bites into the tissue sample 91 without the crushing part 3 being moved upward relative to the support part 30, and the tissue sample 91 is crushed by rotation of the inner blade 31p of the blender 31. On the other hand, in a case where a hard tissue sample 92 such as a cancerous lymph node is to be crushed, even if the crushing part 3 is lowered in a state where the blender 31 comes into contact with the tissue sample 92, the tissue sample 92 hardly deforms. In this state, the blender 31 is strongly pressed against the tissue sample 92. At this time, the spring 39 is compressed by the upward force from the tissue sample 92 received by the blender 31, and the crushing part 3 is moved upward. Here, in a case where the crushing part 3 is moved upward by the distance T, the blender 31 is pressed against the tissue sample 92 with a pressing force F satisfying the relationship of pressing force $F = k \cdot T$. The spring constant k of the spring 39 is set so as not to be excessive such that the pressing force F does not impede the rotation of the blender 31. Thus, a pressure applied to the tissue sample caused by lowering the blender 31 is absorbed by the spring 39. This can avoid the situation where the blender 31 is strongly pressed to the tissue sample and stuck with the tissue sample. The blender 31 is pressed against the tissue sample 92 with the pressing force F, the rotation of the inner blade 31p is maintained. Accordingly, crushing of the tissue sample 92 is promoted and the tissue sample 92 is assuredly crushed.

Figure 8:
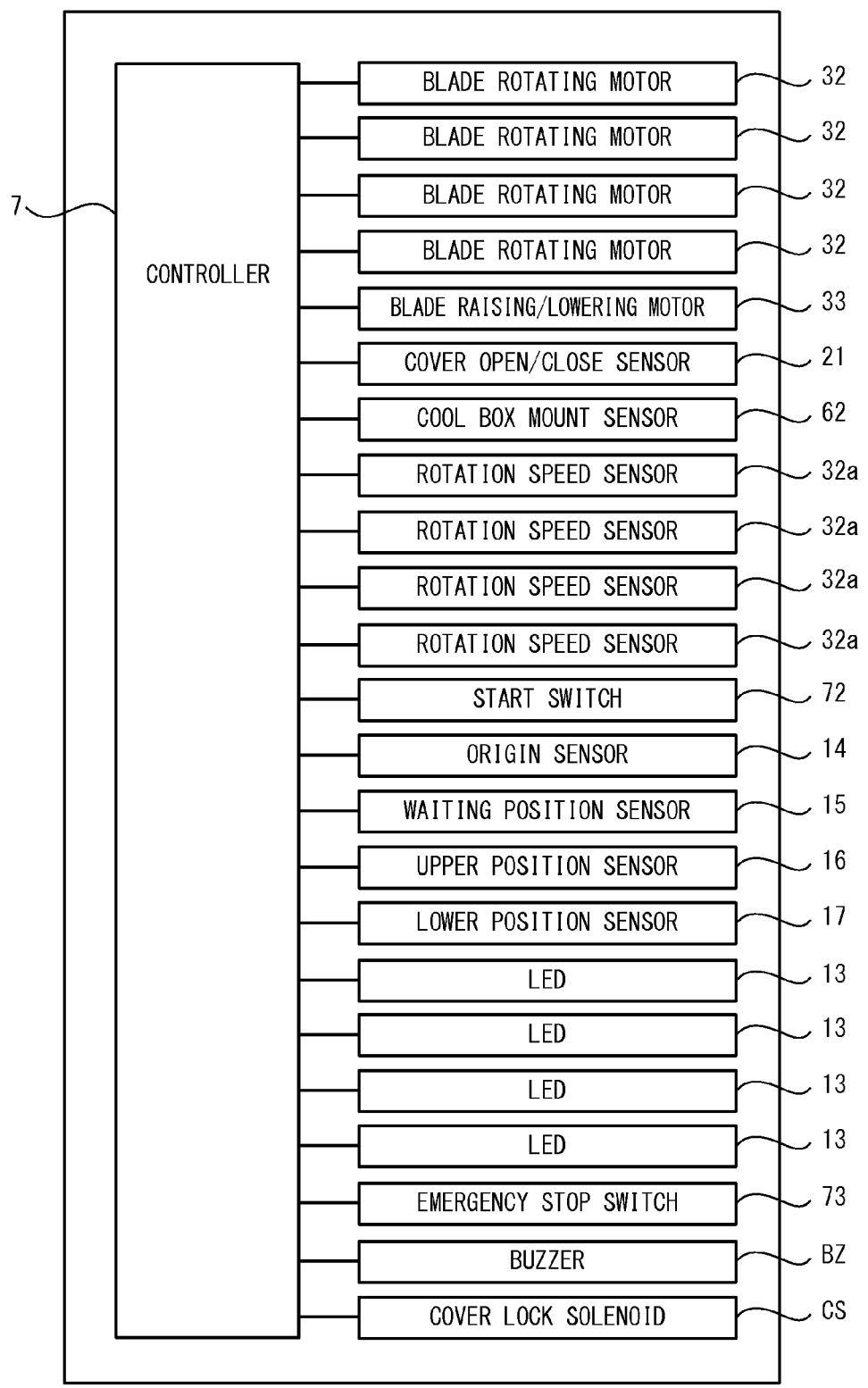
FIG. 8 is a block diagram showing a configuration of an electric circuit of a homogenizer according to an embodiment.

FIG. 8 is a block diagram showing a configuration of an electric circuit of the homogenizer 1 according to the present embodiment. The apparatus body 10 of the homogenizer 1 includes a controller 7 implemented by an FPGA. To the controller 7, the blade rotating motors 32 and the blade raising/lowering motor 33 are connected. The controller 7 can control the blade rotating motors 32 and the blade raising/lowering motor 33. Further, the blade rotating motors 32 are respectively provided with rotation speed sensors 32a. Each rotation speed sensor 32a is configured to detect a rotation speed of a corresponding blade rotating motor 32. Each rotation speed sensor 32a is connected to the controller 7, and can output a detection signal of a rotation speed to the controller 7.

The housing of the apparatus body 10 is provided with a cover open/close sensor 21 being a photo interrupter for detecting that the cover 2 is closed. The cover open/close sensor 21 is connected to the controller 7, and can output a detection signal to the controller 7.

Further, the apparatus body 10 is provided with a cool box mount sensor 62 being a photo interrupter for detecting that the cool box 4 is mounted on the setting part 6. The cool box mount sensor 62 is connected to the controller 7, and can output a detection signal to the controller 7.

The housing of the apparatus body 10 is provided with a start switch 72 and an emergency stop switch 73. As shown in FIG. 1, the start switch 72 and the emergency stop switch 73 are button switches provided on the front face of the apparatus body 10, and are operable by an operator. The start switch 72 and the emergency stop switch 73 are connected to the controller 7 and can provide output signals thereof to the controller 7. When the start switch 72 is operated, the homogenizer 1 starts a crushing process. When the emergency stop switch 73 is operated during the crushing process, the crushing process is suspended.

Further, the raising/lowering mechanism section 18 of the apparatus body 10 is provided with a plurality of photo interrupters for detecting positions in the up-down direction of each crushing part 3 supported by the support part 30. An origin sensor 14 is a photo interrupter for detecting whether each crushing part 3 is at an origin position, and a waiting position sensor 15 is a photo interrupter for detecting whether the crushing part 3 is at a waiting position. The origin position is a position above each sample container 5 held in the cool box 4, and is used for initial position setting of the crushing part 3 in an initialization operation for the homogenizer 1. The waiting position is a position lower than the origin position, and is a position for causing the crushing part 3 to wait before performing a crushing operation of the tissue sample. An upper position sensor 16 is a photo interrupter for detecting whether the crushing part 3 is at a second position. A lower position sensor 17 is a photo interrupter for detecting whether the crushing part 3 is at a first position. The first position is a position of the crushing part 3 where the tip of the blender 31 is located near the bottom portion of the sample container 5. The second position is a position higher than the first position and lower than the waiting position. In the crushing operation of a tissue sample by the blender 31, the crushing part 3 reciprocates between the first position and the second position. Each of the origin sensor 14, the waiting position sensor 15, the upper position sensor 16, and the lower position sensor 17 is connected to the controller 7 and can output a detection signal to the controller 7.

Further, four LEDs 13 are attached to the wall part 19 of the apparatus body 10, in a line along the left-right direction (see FIG. 5). These LEDs 13 are for making notifications of abnormalities in the crushing parts 3, and respectively correspond to the crushing parts 3. The leftmost LED 13 is for making a notification of an abnormality in the leftmost crushing part 3. The LED 13 second from the left is for making a notification of an abnormality in the crushing part 3 second from the left. The LED 13 third from the left is for making a notification of an abnormality in the crushing part 3 third from the left. And the rightmost LED 13 is for making a notification of an abnormality in the rightmost crushing part 3. As shown in FIG. 8, these LEDs 13 are connected to the controller 7, and can be controlled by the controller 7.

Further, a buzzer BZ is provided inside the apparatus body 10 (see FIG. 8). The homogenizer 1 sounds the buzzer when the crushing process has been completed and also when an error has occurred.

The apparatus body 10 is provided with a cover lock solenoid CS for locking the cover 2 closed. The cover lock solenoid CS locks the cover 2 when the start switch 72 is operated, and it unlocks the cover 2 when the crushing process is completed. Accordingly, the cover 2 is prevented from being opened during the crushing process, and thus, safety is improved.

<Operation Performed by Homogenizer>

Next, operations performed by the homogenizer 1 according to the present embodiment will be described.

Figure 9:
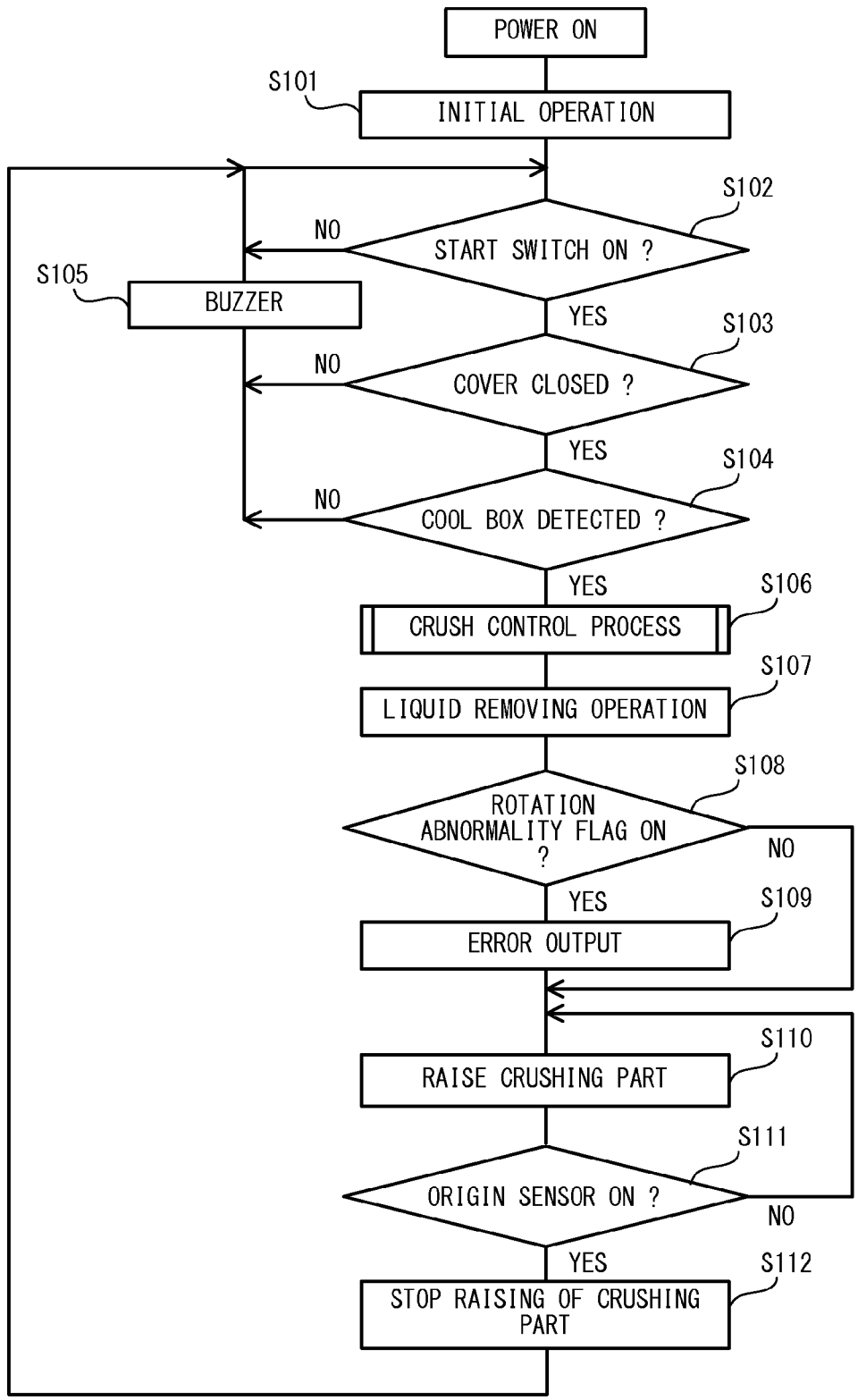
FIG. 9 is a flow chart showing a procedure of operations performed by the homogenizer.

FIG. 9 is a flow chart showing the procedure of operations performed by the homogenizer 1 according to the present embodiment. By performing the process steps shown in FIG. 9, the controller 7 drives the blade raising/lowering motor 33 to raise/lower the crushing parts 3. When the power of the homogenizer 1 is turned on, the processing is started. When the power is turned on, the controller 7 controls the blade raising/lowering motor 33 to perform an initial operation (step S101). In the initial operation, the crushing parts 3 are raised first, until the origin sensor 14 is turned on. When the origin sensor 14 is turned on, the crushing parts 3 are lowered until the waiting position sensor 15 is turned on. Upon the waiting position sensor 15 being turned on, the crushing parts 3 are raised again until the origin sensor 14 is turned on. The initial operation confirms that the raising/lowering operation of the crushing parts 3 can be performed normally.

The controller 7 determines whether the start switch 72 has been turned on (step S102). When an operator turns on the start switch 72, the start switch 72 provides an output signal to the controller 7, whereby the controller 7 detects that the start switch 72 has been turned on. When the start switch 72 is not turned on (NO in step S102), the controller 7 repeats step S102.

On the other hand, in step S102, when it is detected that the start switch 72 has been turned on (YES in step S102), the controller 7 detects whether the cover 2 is closed (step S103). When it is not detected that the cover 2 is closed (NO in step S103), the controller 7 sounds the buzzer BZ in order to notify the operator that the cover 2 is not closed (step S105), and returns the processing to step S102. When it is detected that the cover 2 is closed in step S103 (YES in step S103), the controller 7 advances the processing to step S104.

The controller 7 determines whether the cool box 4 is mounted (step S104). As described above, when the setting part 6 is moved toward the apparatus body 10 side with the cool box 4 mounted on the setting part 6, the cool box mount sensor 62 detects the cool box 4, and outputs a detection signal corresponding to this detection. By receiving this detection signal, the controller 7 detects that the cool box 4 is mounted on the apparatus body 10. In step S104, when it not detected that the cool box 4 is mounted (NO in step S104), the controller 7 sounds the buzzer BZ in order to notify the operator that the cool box 4 is not mounted (step S105), and returns the processing to step S102. When the cool box 4 is mounted, the controller 7 advances the processing to step S106, and performs a crush control process for driving the crushing parts 3 in order to crush the tissue samples (step S106).

Figure 10:
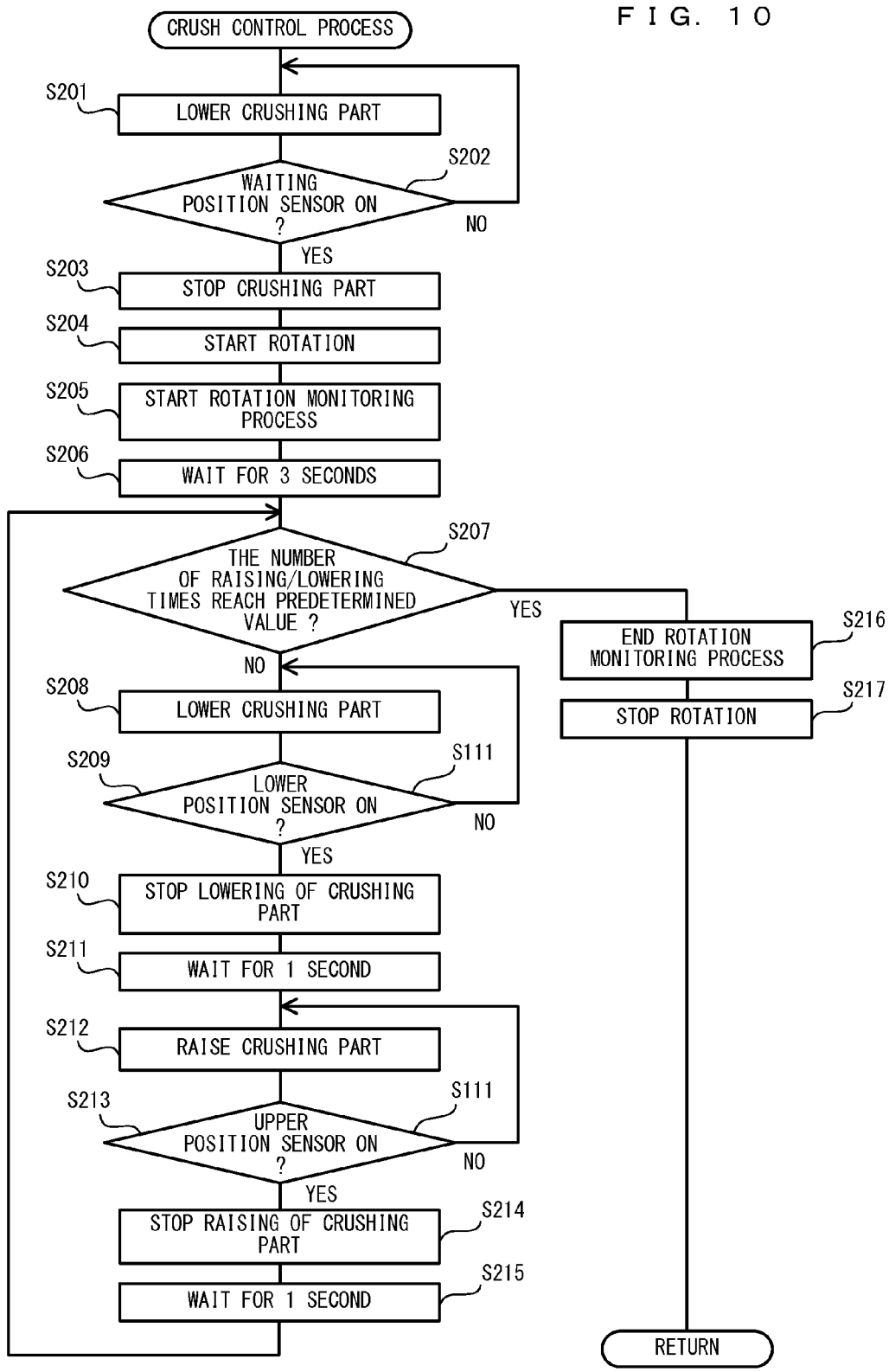
FIG. 10 is a flow chart showing a procedure of a crush control process.

FIG. 10 is a flow chart showing the procedure of the crush control process. Upon the start of the crush control process, in order to close the cover 2, the controller 7 controls the cover lock solenoid CS to lock the cover 2 first, and then causes the crushing parts 3 to be lowered (step S201). The controller 7 determines whether the waiting position sensor 15 has been turned on (step S202). When the waiting position sensor 15 is off (NO in step S202), i.e., the crushing parts 3 are not at the waiting position, the controller 7 returns the processing to step S201 to continue lowering of the crushing parts 3. When the waiting position sensor 15 is turned on in step S202 (YES in step S202), i.e., the crushing parts 3 reaches the waiting position, the controller 7 controls the blade raising/lowering motor 33 to stop lowering of the crushing parts 3 (step S203).

With the crushing parts 3 stopped at the waiting position, the controller 7 controls the four blade rotating motors 32 respectively to start rotation of the inner blades 31p of the corresponding blenders 31 (step S204). As a result of the process of step S204, the inner blades 31p of the blenders 31 rotate at a predetermined rotation speed.

Upon the start of rotation of each crushing part 3 in step S204, the controller 7 starts a rotation monitoring process (step S205) described below. The rotation monitoring process (see, FIG. 11) is performed in parallel with the crush control process. The rotation monitoring process will be described later with reference to FIG. 11. Accordingly, while monitoring whether the inner blade 31p of each blender 31 is normally rotating, the crush control process is performed.

Figure 12:
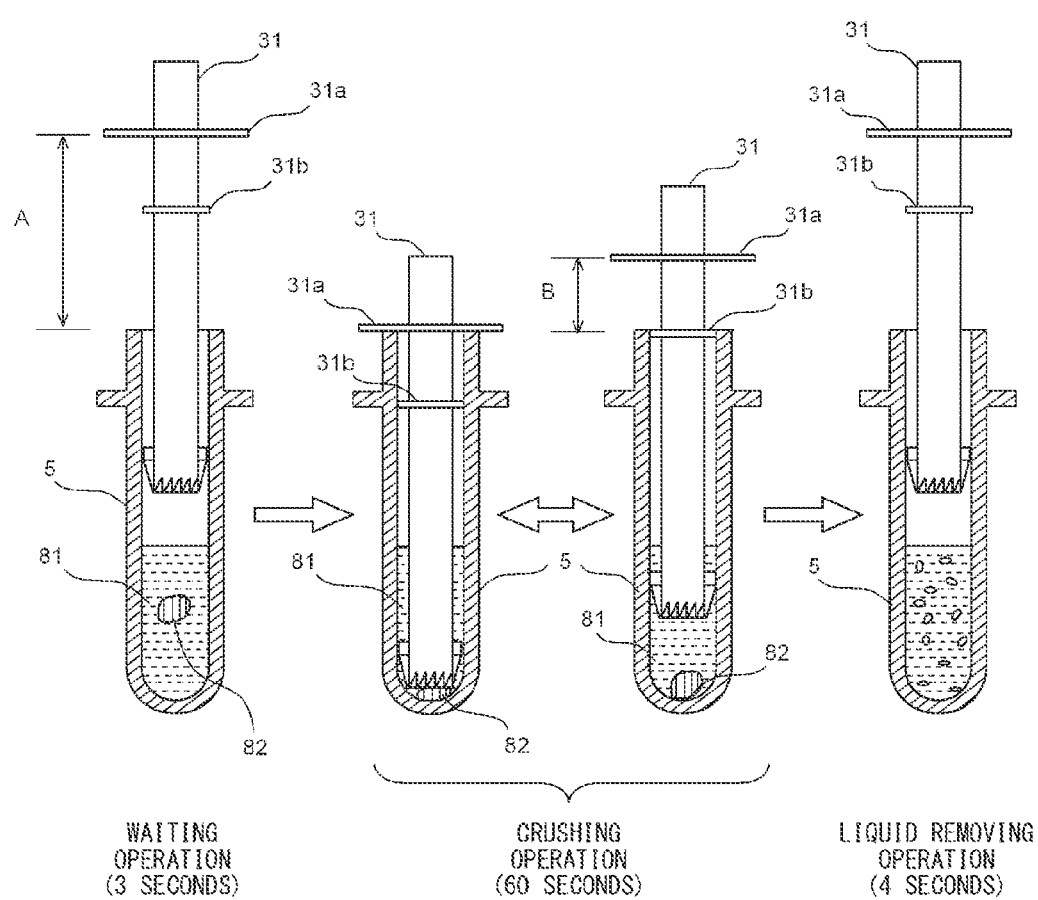
FIG. 12 is a schematic diagram for describing an operation performed by the crushing part.

The controller 7 causes each crushing part 3 to wait for three seconds with the crushing part 3 rotating (step S206). FIG. 12 is a schematic diagram for describing the operation performed by each crushing part 3. The blender 31 is provided with a flange 311a having an annular shape and protruding outward. The outer diameter of the flange 311a is greater than the outer diameter of the opening of the sample container 5. In the waiting operation in step S206, the blender 31 is held for three seconds in a state where the flange 311a is positioned at the waiting position which is higher than the upper end of the sample container 5 by a distance A. At this time, the tip portion of the blender 31 is located near the center portion in the longitudinal direction of the sample container 5, and is above the liquid surface of a lysate 81.

After waiting for three seconds, the controller 7 determines whether the number of raising/lowering times of the crushing part 3 has reached a predetermined value (step S207). In the present embodiment, this predetermined value is 15. When the number of raising/lowering times has not reached the predetermined value (NO in step S207), the controller 7 advances the processing to step S208. In step S208, the controller 7 controls the blade raising/lowering motor 33 to lower the crushing part 3 (step S208). The crushing part 3 is lowered while the inner blade 31*p* of the blender 31 is rotated. The controller 7 determines whether the lower position sensor 17 has been turned on (step S209). When the crushing part 3 is not at the first position and the lower position sensor 17 is still off (NO in step S209), the controller 7 returns the processing to step S208 to continue lowering of the crushing part 3. On the other hand, when the crushing part 3 has reached the first position and the lower position sensor 17 has been turned on in step S209 (YES in step S209), the controller 7 controls the blade raising/lowering motor 33 to stop lowering of the crushing part 3 (step S210). Then, the controller 7 waits in that state for one second (step S211).

The above operation is described with reference to FIG. 12. At the first position, the tip of the blender 31 is located near the bottom portion of the sample container 5. Accordingly, the inner blade 31*p* and the outer blade 31*q* of the blender 31 come into contact with the tissue sample 82, and by the inner blade 31*p* and the outer blade 31*q* rotating relative to each other, the tissue sample 82 is crushed. At the first position, the flange 311*a* of the blender 31 abuts against the upper end of the sample container 5. That is, the opening of the sample container 5 is closed with the flange 311*a*, and thus, scatter of a mixture of the tissue sample and the lysate from the sample container 5 is prevented.

When the tissue sample is hard, even when the crushing part 3 is lowered to the first position, the spring 39 is compressed as described above and the position of the blender 31 is adjusted. That is, even when the crushing part 3 is lowered with a strong force according to an output from the blade raising/lowering motor 33, the spring 39 is compressed, whereby the blender 31 is raised relative to the support part 30. Thus, the blender 31 is pressed against the tissue sample with an appropriate pressing force satisfying F=k·T. Therefore, a situation is avoided where the tissue sample is stuck between the blender 31 and the bottom portion of the sample container 5 to impede the rotation of the blender 31. Accordingly, by the inner blade 31*p* of the blender 31 rotating while the blender 31 is being pressed against the tissue sample with an appropriate pressing force, crushing of the tissue sample is promoted and thus, the tissue sample is assuredly crushed.

After waiting for one second in step S211, the controller 7 controls the blade raising/lowering motor 33 to raise the crushing part 3 (step S212). That is, while the inner blade 31*p* of the blender 31 rotating, the crushing part 3 is raised. The controller 7 determines whether the upper position sensor 16 has been turned on (step S213). When the crushing part 3 is not at the second position and the upper position sensor 16 is still off (NO in step S213), the controller 7 returns the processing to step S212 to continue raising of the crushing part 3. On the other hand, when the crushing part 3 has reached the second position and the upper position sensor 16 has been turned on in step S213 (YES in step S213), the controller 7 controls the blade raising/lowering motor 33 to stop raising of the crushing part 3 (step S214). Further, the controller 7 waits in that state for one second (step S215).

The above operation is described with reference to FIG. 12. At the second position, the tip of the blender 31 is located above the bottom portion of the sample container 5 and below the liquid surface of the lysate. Accordingly, pieces of the crushed tissue sample and the lysate are mixed together, and thus, clogging of the tissue sample between the inner blade 31*p* and the outer blade 31*q* is prevented. The blender 31 is provided with a flange 311*b* having an annular shape, below the flange 311*a*. The outer diameter of the flange 311*b* is set to be slightly smaller than the inner diameter of the sample container 5. When the crushing part 3 is at the second position, the flange 311*b* is located at the upper end of the sample container 5. That is, the opening of the sample container 5 is substantially closed with the flange 311*b*, and thus, scatter of a mixture of the tissue sample and the lysate from the sample container 5 is prevented.

After waiting for one second in step S215, the controller 7 returns the processing to step S207, and determines again whether the number of raising/lowering times of the crushing part 3 has reached the predetermined value (step S207). Until the number of raising/lowering times of the crushing part 3 reaches the predetermined value (15 times), the processes of step S208 to S215 are repeated. When the number of raising/lowering times has reached the predetermined value in step S207 (YES in step S207), the controller 7 ends the rotation monitoring process being performed in parallel with the crush control process (step S216), controls the blade rotating motors 32 to stop rotation of the inner blades 31*p* of the blenders 31 (step S217), and then returns the processing to the main routine.

FIG. 13 is a graph for describing raising/lowering of the crushing part 3 in the crushing operation. In FIG. 13, the vertical axis represents position of the blender 31, and the horizontal axis represents time. As shown in FIG. 13, the blender 31 is held at the first position being the lowest point for about one second, and then is moved to the second position, which is higher than the first position by a distance B. The blender 31 is held at the second position being the highest point for about one second, and then is lowered to the first position. In the crushing operation, such raising/lowering of the crushing part 3 is repeated a predetermined times (15 times). During this time, the inner blade 31*p* of the blender 31 continues to rotate. Such a crushing operation is performed for 60 seconds.

In the crushing operation, each blender 31 performs the rotating operation while reciprocating between the first position and the second position as described above. Thus, the inner blade 31*p* and the outer blade 31*q* of the blender 31 do not stay at a certain position, and accordingly, the mixture of the tissue sample and the lysate is stirred well. Further, pieces of the tissue sample are prevented from being attached to the inner wall of the sample container 5 and held there, and thus, the size of the pieces of the crushed tissue sample becomes uniform.

When the crushing part 3 is at the first position and the inner blade 31*p* of the blender 31 rotates while being pressed against the tissue sample, there may be a case where the inner blade 31*p* is stuck to the tissue sample. If the inner blade 31*p* is stuck to the tissue sample, not only the inner blade 31*p* but also the tissue sample rotate in an integrated manner. This may cause a crushing failure. By repeating raising/lowering of the crushing part 3 as described above, when the crushing part 3 is lowered, the blender 31 is pressed against the tissue sample, and when the crushing part 3 is raised, the blender 31 is separated from the tissue sample. Even in a case where the inner blade 31*p* is stuck to the tissue sample, when the blender 31 is separated from the tissue sample, the integrated rotation of the inner blade 31p and the tissue sample is canceled, and only the blender 31 will rotate. When the crushing part 3 is lowered and pressed against the tissue sample again, the tissue sample is expected to be well crushed, without causing integrated rotation of the inner blade 31p and the tissue sample.

Now, the rotation monitoring process performed by the controller 7 is described. FIG. 11 is a flow chart showing the procedure of the rotation monitoring process. The rotation monitoring process is a process for monitoring that rotation of each crushing part in the crush control process is normally being performed. This process is performed in parallel with the crush control process. It should be noted that the rotation monitoring process is individually performed for each of the four blade rotating motors 32. In addition, the controller 7 has four rotation abnormality flags in an area of a memory included therein. The rotation abnormality flags respectively correspond to the blade rotating motors 32. The flags are used for storing information indicating presence/absence of an abnormality in their corresponding blade rotating motors 32. Each rotation abnormality flag is set to OFF, as an initial value, which indicates that there is no abnormality. When an abnormality in a corresponding blade rotating motor 32 has been detected, the rotation abnormality flag is set to ON, which indicates that an abnormality has occurred.

Upon the start of the rotation monitoring process, the controller 7 determines, based on an output signal from each rotation speed sensor 32a, whether the rotation speed of its corresponding blade rotating motor 32 is less than or equal to a first reference value (step S301). The first reference value is 9500 rotations/second in the present embodiment. When the rotation speed of the blade rotating motor 32 is less than or equal to the first reference value (YES in step S301), the controller 7 determines that an abnormality has occurred in the blade rotating motor 32. The controller sets the rotation abnormality flag corresponding to this blade rotating motor to ON (step S302), and returns the processing to step S301.

When the rotation speed of the blade rotating motor 32 is greater than the first reference value (NO in step S301), the controller 7 determines, based on the output signal from the rotation speed sensor 32a, whether the rotation speed of the blade rotating motor 32 is greater than or equal to a second reference value (step S303). The second reference value is 10500 rotations/second in the present embodiment. When the rotation speed of the blade rotating motor 32 is greater than or equal to the second reference value (YES in step S303), the controller 7 determines that an abnormality has occurred in the blade rotating motor 32. The controller 7 controls the blade rotating motor 32 to stop rotation of the corresponding crushing part 3 (step S304). The controller 7 sets the rotation abnormality flag corresponding to this blade rotating motor to ON (step S305) and suspends the crush control process being performed in parallel with this process (step S306). Then this process ends.

When the rotation speed of the blade rotating motor 32 is less than the second reference value (NO in step S303), the controller 7 returns the processing to step S301 to continue monitoring of rotation of the inner blade 31p of the blender 31. Thus, until the rotation monitoring process ends in step S216 of the crush control process, or until the rotation monitoring process and the crush control process are compulsorily terminated in step S306, the monitoring in steps S301 to 303 is continued.

Now, description is returned to the control process of raising/lowering of the crushing parts shown in FIG. 9. After the crush control process and the rotation monitoring process end, the controller 7 controls the blade rotating motors 32 and the blade raising/lowering motor 33 to perform a liquid removing operation (step S107). In the liquid removing operation, each crushing part 3 is raised to be positioned at the waiting position, and in this state, the inner blade 31p of its corresponding blender 31 is rotated (see FIG. 12). At this time, the tip portion of the blender 31 is located near the center portion in the longitudinal direction of the sample container 5, and above the liquid surface of the lysate. Therefore, pieces of the tissue sample and the lysate attached to the inner blade 31p and the outer blade 31q are removed from the blender 31, and scatter of pieces of the tissue sample and the lysate to the outside of the sample container 5 is prevented. This liquid removing operation is performed for four seconds.

Next, by referring to the rotation abnormality flags, the controller 7 determines whether there is a rotation abnormality flag(s) set to ON (step S108). When there is a rotation abnormality flag(s) set to ON (YES in step S108), the controller 7 controls an LED(s) 13 corresponding to the rotation abnormality flag(s) set to ON, to lit the LED(s) 13 (step S109). That is, for example, when the rotation abnormality flag corresponding to the rightmost blade rotating motor 32 is set to ON, the rightmost LED 13 is lit, whereby the abnormality of this blade rotating motor is notified of. After performing the process of step S109, the controller 7 advances the processing step S110. Also when all the rotation abnormality flags are set to be OFF in step S108 (NO in step S108), the controller 7 advances the processing to step S110.

In step S110, the controller 7 controls the blade raising/lowering motor 33 to raise the crushing part 3 (step S110). The controller 7 determines whether the origin sensor 14 has been turned on (step S111). When the crushing part 3 is not at the origin and the origin sensor 14 is still off (NO in step S111), the controller 7 returns the processing to step S110 to continue raising of the crushing part 3. On the other hand, when the crushing part 3 has reached the origin and the origin sensor 14 has been turned on in step S111 (YES in step S111), the controller 7 controls the blade raising/lowering motor 33 to stop raising of the crushing part 3 (step S112). The controller 7 sounds the buzzer BZ in order to notify the operator that the crushing process have been completed, releases the lock by the cover lock solenoid CS, and returns the processing to step S102.

Other Embodiments

In the above embodiment, a configuration has been described in which the spring 39 is provided between the support part 30 and each crushing part 3 to absorb the pressing force of the blender 31 onto the tissue sample, thereby adjusting the pressing force. However, the present invention is not limited thereto. For example, a rubber elastic body may be provided between the support part 30 and the crushing part 3, and when the blender 31 is pressed against the tissue sample, the rubber elastic body expands or contracts, thereby adjusting the pressing force of the blender 31 applied on the tissue sample. Further, a tension spring may be provided between the support part 30 and the crushing part 3, and when the blender 31 is pressed against the tissue sample, the tension spring expands, thereby adjusting the pressing force of the blender 31 applied on the tissue sample.

Further, instead of a configuration in which the pressing force is adjusted by an elastic body, a configuration may be employed in which the pressing force is controlled by a microprocessor. For example, a pressure sensor which detects a pressure acting on the blender 31 may be provided, and based on the pressure detected by this pressure sensor, the operation of the blade raising/lowering motor 33 may be controlled. Then, when a pressure greater than a predetermined value is detected, the blade raising/lowering motor 33 may be controlled so as to raise the blender 31, and when a pressure less than the predetermined value is detected, the blade raising/lowering motor 33 may be controlled so as to lower or stop the blender 31.

Further, by setting the weight of the crushing part 3 appropriately, the pressing force of the blender 31 applied on the tissue sample may be adjusted by the weight of the crushing part 3 itself, without providing the spring 39. In this case, in the case of a soft tissue sample, the blade tip of the blender 31 bites into the tissue sample under the weight of the crushing part 3 itself, and the tissue sample deforms. Accordingly, occurrence of an excessive pressing force in the crushing part 3 is prevented. In the case of a hard tissue sample, the crushing part 3 is raised relative to the support part 30 against the weight of the crushing part 3 itself, and the blender 31 will be pressed against the tissue sample, not under an excessive pressing force from the blade raising/lowering motor, but under the weight of the crushing part 3 itself.

Further, in the above embodiment, the crushing parts 3 are individually provided with the springs 39, respectively, but the present invention is not limited thereto. A configuration may be employed in which: the crushing parts 3 are fixed together; a unit of the crushing parts 3 fixed together is supported so as to be movable in the up-down direction by means of the support part; and an elastic body is provided between the unit of the crushing parts 3 and the support part. In this case, when one crushing part 3 has received a great force from its corresponding tissue sample, and even if the other crushing parts 3 have not received a great force, the elastic body deforms and thus the unit of the crushing parts 3 is raised relative to the support part. Accordingly, the pressing force of the crushing parts 3 is adjusted.

Alternatively, an elastic body may be provided between the sample containers 5 and the apparatus body 10, whereby the pressing force of the crushing parts 3 may be adjusted. In this case, when the crushing parts 3 are pressed against the tissue samples, the relative positional relationship between the sample containers 5 and the apparatus body 10 changes (i.e., the sample containers 5 are lowered relative to the apparatus body 10), and the elastic body deforms, whereby the pressing force of the crushing parts 3 is adjusted.

Further, in the above embodiment, the configuration has been described in which: the cool box 4 vertically holds the sample containers 5; and the crushing parts 3 are lowered in the vertical direction to enter the inside of the sample containers 5. However, the present invention is not limited thereto. The cool box may hold the sample containers in a direction inclined relative to the vertical direction, and the crushing parts may be configured to be able to move along a direction inclined by the same angle as the inclined angle of the sample containers. Then, the crushing parts may be caused to enter the inside of the inclined sample containers.

The invention claimed is:

1. A homogenizer comprising:
a crushing part comprising a shaft, a blender for crushing a tissue sample in a container, and an attachment part connected between the shaft and the blender and having a diameter larger than that of the shaft;
a first driver configured to rotate the blender in contact with the tissue sample;
a support part supporting the crushing part and having a hole through which the shaft of the crushing part passes such that the crushing part is movable relative to the support part;
a second driver configured to move the support part in a first direction to insert the crushing part into the container; and
a spring being provided between the support part and the attachment part of the crushing part, wherein
the crushing part moves relative to the support part in a second direction opposite to the first direction when the blender is pressed against the tissue sample in the container, and the spring contracts according to the movement of the crushing part in the second direction, and
the blender is pressed against the tissue sample in the container with an elastic force of the spring.

2. The homogenizer according to claim 1, wherein
the second driver reciprocates the support part in the first direction and the second direction thereof.

3. The homogenizer according to claim 1, further comprising:
a controller configured to control the first and second drivers such that the blender reciprocates in the container while rotating.

4. The homogenizer according to claim 3, wherein
when crushing of the tissue sample by the blender is terminated, the controller controls the second driver to move the crushing part in the second direction, and controls the first driver to rotate the blender at a position away from the tissue sample in the container.

5. The homogenizer according to claim 1, further comprising:
a container holder including a plurality of holders each capable of holding a container, wherein
a pair of the crushing part and the first driver is provided for each of the plurality of holders, and
the spring is provided for each of the plurality of the crushing parts.

6. The homogenizer according to claim 1, wherein
the blender has an inner blade and an outer blade, and
the first driver rotates either one of the inner blade and the outer blade relative to the other.

7. The homogenizer according to claim 1, further comprising:
a controller; and
a detector configured to detect the number of rotations of the blender, wherein
the controller controls the first driver to stop rotation of the blender when the number of the rotations is outside a predetermined range.

8. The homogenizer according to claim 7, further comprising:
a container holder including a plurality of holders each capable of holding a container, wherein
a plurality of pairs of the crushing part and the first driver are provided so as to correspond to the container holder, and
in a case where the number of rotations of a blender driven by one of the first drivers is outside the predetermined range, the controller stops the first driver and causes the other first drivers to continue driving.

9. The homogenizer according to claim 7, further comprising:
a notification part for making a notification of an abnormality, wherein
in a case where the number of rotations of the blender is smaller than a lower limit value of the predetermined range, the controller causes the blender to continue rotating and controls the notification part to output a notification of an abnormality after completion of the rotation.

10. The homogenizer according to claim 1, wherein
the plurality of the crushing parts are supported by the support part, and
the second driver moves the plurality of the crushing parts simultaneously by moving the support part.

11. The homogenizer according to claim 1, wherein the blender is detachably attached to the attachment part of the crushing part.

* * * * *